(12) United States Patent
Mullen et al.

(10) Patent No.: US 8,373,862 B2
(45) Date of Patent: Feb. 12, 2013

(54) EXTENDED RANGE OPTICAL IMAGING SYSTEM FOR USE IN TURBID MEDIA

(75) Inventors: Linda J. Mullen, Chesapeake Beach, MD (US); Alan Laux, Great Mills, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 520 days.

(21) Appl. No.: 12/792,183

(22) Filed: Jun. 2, 2010

(65) Prior Publication Data

US 2012/0069341 A1    Mar. 22, 2012

(51) Int. Cl.
*G01N 21/55* (2006.01)
(52) U.S. Cl. ............ 356/445; 348/67; 382/211
(58) Field of Classification Search ............ None
See application file for complete search history.

(56) References Cited

U.S. PATENT DOCUMENTS

| | | | |
|---|---|---|---|
| 5,446,529 A * | 8/1995 | Stettner et al. | 356/4.01 |
| 5,822,047 A | 10/1998 | Contarino et al. | |
| 6,041,248 A * | 3/2000 | Wang | 600/407 |
| 7,006,676 B1 * | 2/2006 | Zeylikovich et al. | 382/131 |
| 7,010,339 B2 | 3/2006 | Mullen et al. | |
| 2008/0218821 A1 | 9/2008 | Dalgleish | |
| 2008/0219584 A1 * | 9/2008 | Mullen et al. | 382/264 |
| 2009/0115967 A1 | 5/2009 | Gerlach | |

OTHER PUBLICATIONS

De Dominicis et al., Improving Underwater imaging in an amplitude modulated laser system with radio frequency control technique, Journal of the European Optical Society—Rapid Publications 5, 2009, 5 pages.*

Pellen et al., Radio Frequency Modulation on an optical carrier for target detection enhancement in seawater, J. Phys. D Appl. Phys. 34, 1122-1130, 2001.*

Austin, Roswell W., Duntley, S. Q., Ensminger, R. L., Petzold, T. J., Smith Raymond C., "An Underwater Laser Scanning System," SPIE vol. 1537 Underwater Imaging, Photography, arid Visibility (1991), pp. 57-73, International Society for Optics and Photonics, Bellingham WA USA.

Ricci, R., Francucci, M., De Dominicis, L., Ferri De Collibus, M., Fornetti, G., Guarneri, M., Nuvoli, M., Paglia, E., Bartolini, L., "Techniques for effective optical noise rejection in amplitude-modulated laser optical radars for underwater three-dimensional imaging," Journal on Advances in Signal Processing, vol. 2010 (2010), Article ID 958360, 24 pages doi:10.1155/2010/958360, Hindawi Publishing Corporation, 410 Park Avenue, 15th Floor, #287 pmb, New York, NY 10022 USA.

(Continued)

*Primary Examiner* — Gregory J Toatley
*Assistant Examiner* — Juan D Valentin, II
(74) *Attorney, Agent, or Firm* — Mark O. Glut; Mark D. Kelly

(57) ABSTRACT

An extended range optical imaging system and method for use in turbid media generates a beam of coherent light, modulates the beam of coherent light to encode scan information, directs the modulated beam of coherent light from a first location through the turbid medium toward a target, scans the modulated beam of coherent light over the target in a pattern, according to the scan information, to illuminate the target and to cause light to be reflected, detects the modulated light reflected from the target with a sensor at a second location in the turbid medium to derive an output signal that varies in proportion to the modulated reflected light, demodulates the output signal to derive information comprising the scan information, and constructs an image from the output signal and the scan information so derived.

26 Claims, 2 Drawing Sheets

OTHER PUBLICATIONS

Kulp, Thomas J., Garvis, Darrel, Kennedy, Randall, Salmon, Tom, Cooper, Keith, "Development and testing of a synchronous-scanning underwater imaging system capable of rapid two-dimensional frame imaging," Applied Optics / vol. 32, No. 19, pp. 3520-3530 / Jul. 1, 1993, Optical Society of America, 2010 Massachusetts Ave., N.W., Washington, D.C. 20036-1012 USA.

S. Q. Duntley, W. Austin, R. L. Ensminger, T. J. Petzold, and R. C. Smith, "Experimental TVI system report: Part I, Jul. 1974; Part II, Oct. 1974," Tech. Rep. 74-1 (Scripps Visibility Laboratory, Scripps Institute of Oceanography, University of California, San Diego, La Jolla. CA., USA 1974).

* cited by examiner

EXTENDED RANGE OPTICAL IMAGING SYSTEM FOR USE IN TURBID MEDIA

GOVERNMENT INTEREST

The invention described herein may be manufactured, licensed, and used by or for the U.S. Government.

BACKGROUND

In general, the intensity of light in a transmissive media decays exponentially. Over a round-trip path, the intensity of a beam of light is attenuated by $e^{-2cr}$ where c is the total attenuation coefficient of the medium, and r is the distance from source to target. The distance at which light is attenuated by $e^{-1}$ is referred to as an attenuation length (AL). In clear water this distance is between 20 to 30 meters, and even less in a turbid media such as ocean water, clouds, fog, smoke or tissue. This places practical limits on underwater optical imaging. At distances beyond about three AL, laser-based systems are typically used to image underwater targets. The U.S. Navy has been continuously developing underwater imaging systems for use in a variety of applications including Autonomous Underwater Vehicles (AUVs) and Remotely Operated underwater Vehicles (ROVs) to provide navigational data as well as other data for detecting the presence of mines and AUV's and ROV's.

Imaging theory based on the Modulation Transfer Function (MTF) predicts that an ideal self-luminous source can be detected well over 15 AL under nighttime observation, depending on the source size. In order to attempt to reach this theoretical limit, the engineering task therefore becomes one of designing a system that can extract target detail as a sequence of discrete self-luminous sources. One way to do this is to bring a laser source as close to a target as possible. However, a nearby laser source that illuminates the entire target at the same time is not the answer. Scattering due to particles along the path between the target and a distant receiver (a separate unit from the laser source) will mix photons between neighboring pixels together and the target will become unrecognizable after a half-dozen attenuation lengths. Under these circumstances, a better imaging system, especially for turbid media, is one that makes use of an "illuminator" which scans each of the target "pixels" in a predetermined sequence as closely as possible to the target. The scanning of the target will produce a time-varying intensity (TVI) signal at the distant receiver that is not adversely affected by scattering. This is due to the fact that since the laser illuminates only a small portion of the target of interest at a time, all of the light that is reflected by the scene at each scan position—even the multiply scattered light—carries "useable" information about the target. Thus, the receiver can collect all of the light reflected by each pixel in the scene and still produce high quality images over many attenuation lengths. An image of the target and its details can then be reconstructed remotely (e.g., onboard a nearby ship) as long as the predetermined scanning sequence used for target illumination is known.

Such a system was built in the early 1970's at the Scripp's Visibility Laboratory and experimental data collected by this prototype system confirmed the soundness of the approach and an associated imaging capability of between 15 and 20 attenuation lengths at 640 nm. See, S, Q, Duntley, R. W. Austin, R. L. Ensminger, T. J. Petzold, and R C. Smith, "Experimental TVI System Report," Visibility Laboratory Technical Report 74-1, Part I, July, 1974 and Part II, October 1974. A flash lamp co-located with the laser source produced an optical signal that was used for synchronization. The flash of light indicated the beginning of a scan, and the remote receiver synchronized its data collection with this optical trigger. This system produced impressive underwater images at greater than 20 attenuation lengths in turbid harbor water.

A drawback of this system was that a separate flash lamp source was needed to convey the start of a scan to the distant receiver. Moreover, this was the only information that the receiver had concerning the scan. Therefore, certain things had to be assumed by the receiver, such as standoff distance, scan rate, and scan angle, so that it could correctly recreate the image. Another disadvantage was the fact that this initial system used a red laser with a wavelength of 640 nm. Better performance is generally expected with a laser in the blue-green region of the optical spectrum due to the lower absorption at shorter wavelengths. Finally, two optical receivers were needed in order to separate the laser light reflected from the scene of interest from the flash lamp used to synchronize the beginning of the scan. Embodiments according to the present invention are directed to solving the foregoing problems.

SUMMARY

In general, in one aspect, a method for optically imaging a target in a turbid medium, includes generating a beam of coherent light, modulating the beam of coherent light to encode scan information, directing the modulated beam of coherent light from a first location through the turbid medium toward the target, scanning the modulated beam of coherent light over the target in a pattern, according to the scan information, to illuminate the target and to cause light to be reflected, detecting the modulated light reflected from the target with a sensor at a second location in the turbid medium to derive an output signal that varies in proportion to the modulated reflected light, demodulating the output signal to derive information comprising the scan information; and constructing an image from the output signal and the scan information so derived.

In general, in another aspect an apparatus to optically image a target in a turbid medium, includes a source of coherent electromagnetic energy that emits a beam that is transmissible in a turbid medium, a modulator to modulate the beam of electromagnetic energy with information comprising scan information, a scanner to direct the beam through the turbid medium and to scan the beam over the target, a detector to detect the electromagnetic energy reflected from the target and to output a signal, a demodulator to demodulate the output signal from the detector and to derive information comprising the scan information, an analog to digital converter to digitize the demodulated output signal from the detector; and an image processor to convert the digitized signal from the analog to digital converter to a grayscale image.

Unless otherwise defined, all technical and scientific terms used herein have the same meaning as commonly understood by one of ordinary skill in the art to which this invention belongs. Other features and advantages will be apparent from the following detailed description.

BRIEF DESCRIPTION OF THE DRAWINGS

Exemplary embodiments according to the invention are illustrated in the accompanying drawings in which like reference numerals represent like parts throughout and in which.

DETAILED DESCRIPTION

In the following detailed description, reference is made to the accompanying drawings which are a part of this patent disclosure, and in which are shown by way of illustration specific embodiments in which the invention, as claimed, may be practiced. This invention may, however, be embodied in many different forms and should not be construed as limited to the embodiments set forth; rather, these embodiments are provided so that this disclosure will be thorough and complete, and will fully convey the scope of the invention to those skilled in the art.

Figure 1:
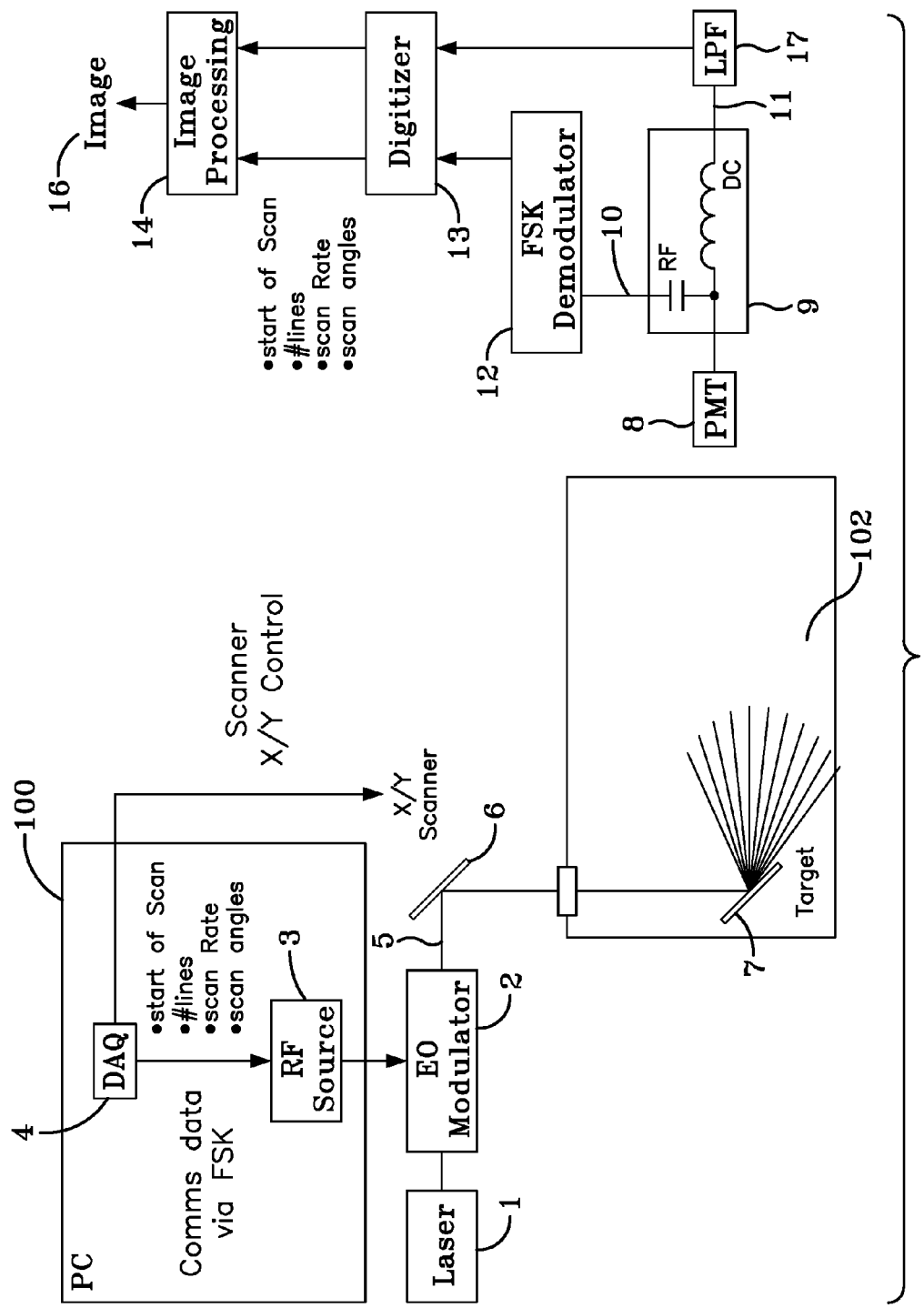
FIG. 1 is a block diagram of a first exemplary embodiment of an extended range optical imaging system for use in turbid media, according to the invention.

A diagram of a laboratory prototype embodiment according to the invention is shown in FIG. 1. A blue-green laser 1 is intensity modulated by an external electro-optic (EO) modulator 2 to produce a modulated laser beam 5. The modulated laser beam 5 is directed to a scanner 6, for example, a galvanometer scanner, which scans the beam 5 in a pattern over a target 7 located in a turbid medium 102. In the laboratory prototype, the turbid media 102 is water to which Maalox antacid has been added, to simulate scattering in seawater. Although a wide variety of lasers would work, lasers that operate in the blue or blue-green wavelength region are most suitable for underwater imaging applications and are thus preferred. In this embodiment laser 1 is a 532 nm green diode pumped solid state continuous wave laser. 532 nm lasers are relatively inexpensive and readily available. In alternative embodiments, other types of lasers, which may be continuous or pulsed, and of other wavelengths, may be employed.

The EO modulator 2 is driven by a radio frequency (RF) source 3. The RF source 3 in this embodiment operates at a carrier frequency of 70 MHz. Other carrier frequencies could be used depending on the capabilities of the modulator and the bandwidth needs of a particular embodiment. RF source 3 is modulated with scan information. The scan information includes a line delimiter which may be encoded as a phase shift, a frequency shift, a symbol, or a combination of any of the foregoing. Scan information may also include, for example, indicia of the start and/or the end of the scan or of a scan line, the number of lines, the scan rate and scan angles. As will be described below, a variety of other information may also be added in alternative embodiments. Modulation is performed preferably via frequency shift keying (FSK) or phase shift keying (PSK). Techniques based on modulating the amplitude of the RF source are not used since the amplitude of the RF envelope will be modulated by the reflectivity of the underwater object.

In the laboratory prototype constructed according to the present invention, control functions are performed using National Instrument Company's LabVIEW®, a software program that runs on a general purpose computer (PC) 100 and provides a wide variety of virtual test and measurement instruments. The virtual instruments are capable of interfacing with various I/O devices. In this embodiment, LabVIEW® operates a Data Acquisition (DAQ) device 4, which is a PCI (Peripheral Component Interconnect) card installed in the PC 100 that outputs the FSK modulation to drive RF source 3. In this embodiment scan parameters (number of lines, scan rate, scan angles, etc.) are input by an operator into the LabVIEW® program. The scan parameters and DAQ device 4 are also used to control scanner 6 that directs the modulated laser beam 5 in a predetermined pattern over the target 7. At the beginning of every scan and at the end of every scanned line, the frequency of the RF source 3 is changed. In other embodiments, as noted, the phase might be shifted, or an alternative modulation symbol might be inserted to designate scan lines or other scan information. While LabVIEW® is well suited for use in a laboratory test environment, specialized software and hardware will perform the modulation, synchronization, scanning and image processing functions in embodiments designed for use in the field.

At some distance from target 7 in the turbid media 102, a photon detector 8 detects the light scattered from target 7. Photon detector 8 outputs a signal that varies proportionately with the intensity of the collected light. While a photomultiplier tube (PMT) is presently the device most suited to this application, newly developed highly sensitive solid state photon detectors/counters show promise, for example, silicon "SiPM" devices built from avalanche photodiode arrays. As such devices become commercially available they may be employed in alternative embodiments. The output signal from photon detector 8 is split into an RF component 10 and a DC component 11 via a splitter 9, which may be, for example, a bias tee. The DC component 11 is conditioned by passing it through a low pass filter 17. The RF component 10 is demodulated by an FSK demodulator 12 and digitized by an analog-to-digital converter (A/D) 13 to retrieve the information that was encoded on the modulated laser beam 5 (i.e., start of scan, number of lines, scan rate, scan angles, etc.). The DC component 11, which contains the reflectivity information from the target 7, is also digitized by the A/D 13. A voltage-to-grayscale image conversion processor 14 then converts the DC digitized signal to grayscale levels. The frequency of the RF component 10 is processed to decode the beginning of the scan as well as the end of each scanned line. Images 16 are then created from the grayscale levels output by the grayscale image conversion processor 14. Separate images may be derived from both the DC and the RF components. In the laboratory embodiment where interference from other sources of light is not a problem, only the DC component need be processed to construct images.

Figure 2:
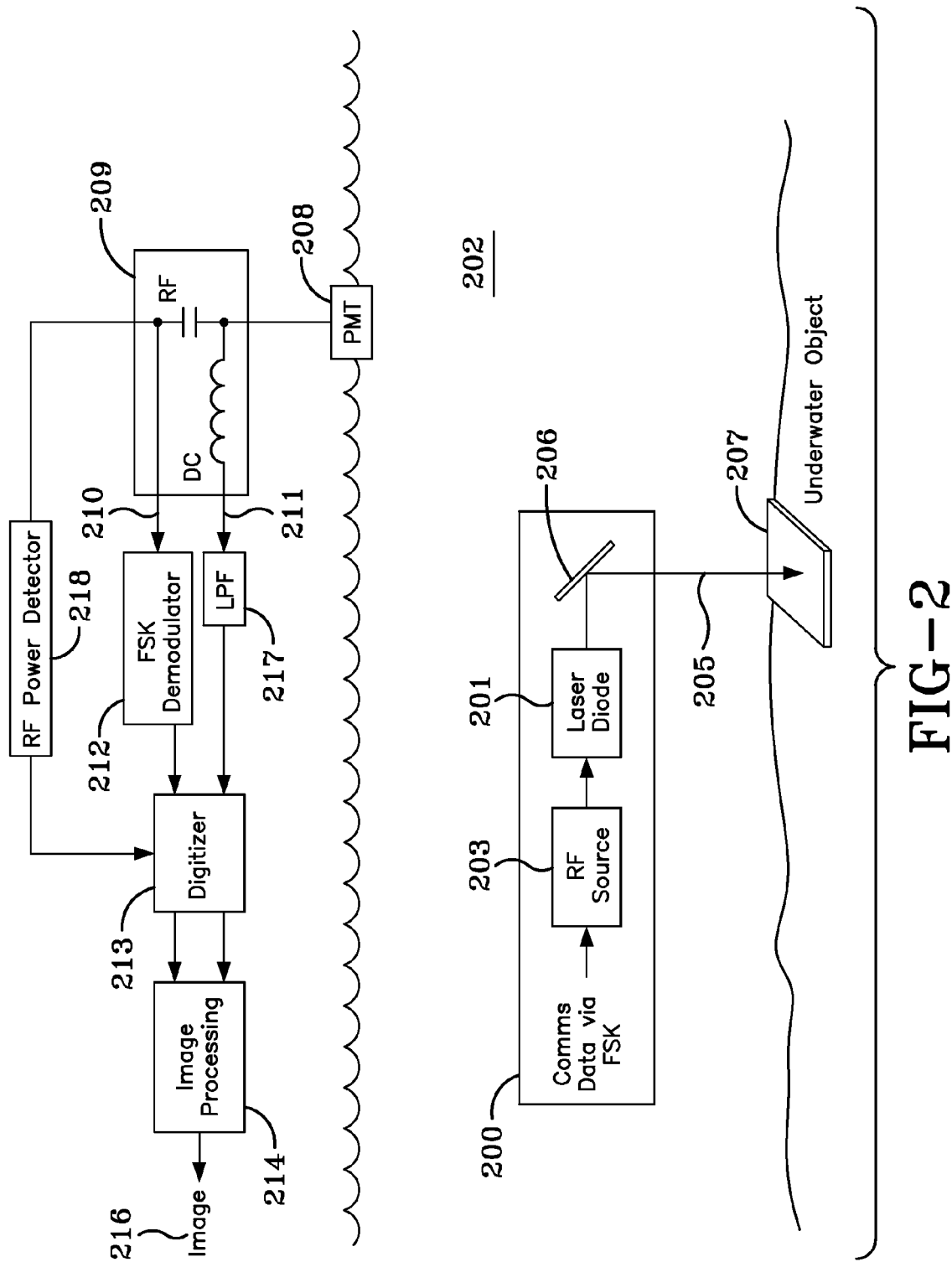
FIG. 2 is a block diagram of a second exemplary embodiment of an extended range optical imaging system for use in turbid media, according to the invention.

FIG. 2 shows an alternative embodiment in which a laser diode source 201 is current modulated by an RF source 203. Here, an imaging system includes a processor 200, which may be an embedded computer that is part of an Autonomous Underwater Vehicle (AUV) or a Remotely Operated Vehicle (ROV), a general purpose computer that is carried on board, a microcontroller or a digital signal processor. Processor 200 may be incorporated in a submersible vehicle or a stationary platform. Processor 200 provides modulation encoded data to RF source 203. As in the previous embodiment, RF source 203 is modulated with scan information via FSK. Other modulation schemes (other than amplitude modulation) may also be used in alternative embodiments. In this embodiment a 10 MHz subcarrier frequency has been used to match the capabilities of presently available laser diode sources 201. Other subcarrier frequencies may be employed depending on the bandwidth requirements of the application, as well as the characteristics and capabilities of laser diode sources 201 that are available. While direct modulation of the laser diode 201 is shown in this embodiment, other methods of modulating the laser diode 201 for example, an external acousto-optic modulator or an electro-optic modulator, may also be employed in alternative embodiments.

The modulated laser beam 205 is transmitted to a scanner 206, for example, an X/Y galvanometer, which scans beam 205 over an underwater target 207 that is submerged in a turbid medium 202. As in the previous embodiment, scan lines are delineated by a frequency change in the modulation, or alternatively, by a phase change or another modulation symbol or symbols.

At a distance of several AL's in the turbid medium 202, a photon detector 208 (preferably a PMT) detects the light scattered from the underwater target 207 and outputs a signal that varies in amplitude in proportion to the intensity of the detected light. The output signal from photon detector 208 is then split into an RF component 210 and a DC component 211 via a splitter 209 (preferably a bias tee). As in the previous embodiment, the DC component 211 is conditioned by passing through a low pass filter 217. In this embodiment, RF component 210 takes two paths. In one path, the RF component 210 is demodulated by an FSK demodulator 212 and digitized by an analog-to-digital converter (A/D) 213 to retrieve the information that was coded on the transmitted waveform (start of scan, number of lines, scan rate, scan angles, etc.). In the other path, the amplitude of the RF component 210, which contains the reflectivity information from the target, is detected via an RF power detector 218 and is digitized by A/D 213.

The DC component 211, which contains the reflectivity information from the target 207, is simultaneously digitized by the A/D 213. This digitized DC signal is monitored to ensure that the photon detector 208 operates in a linear portion of its dynamic range. A voltage to grayscale image conversion processor 214 converts the digitized signals from the RF power detector 218 to grayscale levels. An image 216 is then created from the grayscale levels output by the grayscale image conversion processor 214. In this embodiment, the amplitude of the modulation envelope of the RF signal is preferably used to create the image instead of the DC-coupled signal since the RF signal modulation envelope is not affected by changes in the ambient light level which can frequently take place in the field. As in the first embodiment, the encoded information that was retrieved via the FSK demodulator 212 is also used to construct the target images 216.

Embodiments of an extended range optical imaging system for use in a turbid media according to the present invention offer substantial benefits over the existing approaches. One distinct advantage is that modulation of the laser source may be used to provide the synchronization signal that informs the remote receiver that a scan has been initiated. Therefore, the scattered light itself contains the synchronization information instead of relying on a separate optical trigger. The modulation may also be used to communicate information about the scan. For example, the modulation phase may be varied on a pixel-by-pixel or a line-by-line basis so that the receiver can more accurately construct the images. The modulation phase may also be processed to obtain target range information to create three-dimensional images. Additional "comm" data may also be encoded in the laser depending on bandwidth capabilities of the laser/modulator. For example, position reports as well as command and control communications including velocity, timing and status, may be communicated to, from or among autonomous underwater vehicles as well as other underwater platforms that incorporate systems according to the present invention.

Other information besides the scan details could also be conveyed via the RF modulation, such as location of the laser illuminator relative to the area being surveyed. It is also possible to establish a direct communications link between the laser illuminator and the distant receiver (without reflecting first off of the underwater target). This may be particularly useful in scenarios where the underwater target has very low contrast and the signal reflected from the underwater target is very weak. This "communications only" signal could be transmitted via diffuse light (as is the case when the light is reflected from a diffuse object), which reduces the pointing and tracking requirements on an underwater optical communications link.

Additionally, in alternative embodiments, multiple AUV's may each be equipped with an imaging light source according to the present invention. Each AUV would be provided with its own uniquely identifiable illuminator, to enable coordinated and rapid inspection of a region of interest. By assigning different modulation frequencies or by providing each AUV with a unique identifier, a single remote receiver may discriminate among them and construct composite images. AUV's could also detect and process modulated light signals from other units in the vicinity and thereby avoid collisions with them, as well as receive data concerning the location of hazards detected by other AUV's such as mines. Additionally, an array of scanning lasers may be directed at one or more targets from a single location.

Although the embodiments illustrated in FIGS. 1 and 2 employ continuous wave lasers, a modulated, pulsed source could also be used instead of the modulated continuous wave sources described here. All-digital approaches could also be used that would replace the RF splitter, power detector, and FSK demodulator with a high speed A/D and a digital demodulator.

CONCLUSION

As has been shown, embodiments according to the invention may be used to provide high quality images of targets submersed in a turbid media over an extended range. Accordingly, the scope of the invention should be determined by the following claims and their legal equivalents.

What is claimed is:

1. A method for optically imaging a target in a turbid medium, comprising:
   generating a beam of coherent light from a source;
   modulating the beam of coherent light with encoded information comprised of line delimiters and/or comms data;
   directing the modulated beam of coherent light from a first location through the turbid medium toward the target;
   scanning the modulated beam of coherent light comprising the encoded information over the target in a pattern, to illuminate the target and to cause light to be reflected;
   detecting the modulated light reflected from the target with a sensor at a remote location with no physical connection to the source to derive an output signal that varies in proportion to the modulated reflected light;
   demodulating the output signal and decoding the encoded information; and
   constructing an image from the output signal and the decoded information so derived.

2. The method according to claim 1 further comprising splitting the output signal into an RF component and a DC component.

3. The method according to claim 2, wherein the DC component is monitored to determine whether the detector is operating in a linear range.

4. The method according to claim 2, further comprising employing a modulation envelope of the RF signal to construct the image.

5. The method according to claim 2 further comprising splitting the RF component into a path that is demodulated and a path that is detected by an RF power detector.

6. The method according to claim 5 further comprising a grayscale conversion processor to convert a signal from the RF power detector to grayscale levels.

7. The method according to claim 2, wherein the DC component is monitored to ensure that the detector is operating in a linear range.

8. The method according to claim 1 wherein the coherent beam of light is phase modulated to improve construction of the image.

9. The method according to claim 1 wherein the coherent beam of light is phase modulated to enable processing at the receiver to obtain target range information.

10. The method according to claim 9 wherein the target range information is employed to construct three dimensional images.

11. The method according to claim 1 wherein demodulating the output signal and decoding the encoded information comprises employing a digital demodulator.

12. The method according to claim 1 wherein a plurality of beams of coherent light are generated by a plurality of underwater autonomous vehicles, each beam having a unique identifier, such that a single remote receiver is able to discriminate among the underwater autonomous vehicles.

13. The method according to claim 12 wherein the unique identifier comprises a modulation frequency.

14. A method for optically imaging a target in a turbid medium, comprising:
    generating a beam of coherent light from a source;
    modulating the intensity of the beam of coherent light driven by a radio frequency modulation signal;
    encoding the radio frequency modulation signal with information comprised of line delimiters and/or comms data;
    directing the modulated beam of coherent light from a first location through the turbid medium toward the target;
    scanning the modulated beam of coherent light comprising the encoded information in a predetermined pattern over the target to illuminate the target and cause modulated light to be reflected therefrom;
    detecting the modulated light reflected from the target at a remote location with no physical connection to the source in the turbid medium to derive an output signal that varies in proportion to the modulated reflected light;
    demodulating the output signal and decoding the encoded information; and
    constructing an image from the output signal and the decoded information so derived.

15. The method for optically imaging a target in a turbid medium according to claim 14 wherein the output signal comprises an RF component and a DC component.

16. The method for optically imaging a target in a turbid medium according to claim 15 wherein the DC component of the output signal is monitored to determine whether the detector is operating in a linear range.

17. The method for optically imaging a target in a turbid medium according to claim 15 wherein the RF component of the output signal is employed to construct the image.

18. The method for optically imaging a target in a turbid medium according to claim 14 further comprising processing the detected light to obtain target range information.

19. The method for optically imaging a target in a turbid medium according to claim 14 further comprising encoding command and control communications to and from an autonomous underwater vehicle.

20. The method for optically imaging a target in a turbid medium according to claim 19 wherein a plurality of distinct radio frequency modulation signals are employed to identify and distinguish communications from a plurality of autonomous underwater vehicles.

21. An apparatus to optically image a target in a turbid medium, comprising:
    a source of coherent electromagnetic energy that emits a beam that is transmissible in a turbid medium;
    a modulator driven by a radio frequency modulation signal to modulate the beam of electromagnetic energy;
    an I/O device for modulation of a RF signal which encodes the radio frequency modulation signal with information comprised of line delimiters and/or comms data;
    a scanner to direct the beam through the turbid medium and to scan the beam over the target;
    a detector located at a remote location with no physical contact to the source of coherent electromagnetic energy to detect the electromagnetic energy reflected from the target and to output a signal;
    a demodulator to demodulate the output signal from the detector;
    an analog to digital converter to digitize the demodulated output signal from the detector; and
    an image processor to decode the encoded information and convert the digitized signal from the analog to digital converter to a grayscale image.

22. The apparatus according to claim 21 wherein the beam is frequency modulated.

23. The apparatus according to claim 21 wherein the source of coherent electromagnetic energy comprises a laser.

24. The apparatus according to claim 21 wherein the detector comprises a photomultiplier tube.

25. The apparatus according to claim 21 further comprising a radio frequency power detector to monitor the signal from the detector to ensure that the detector operates in the linear range.

26. An apparatus to optically image a target in a turbid medium, comprising:
    a source of coherent electromagnetic energy that emits a beam that is transmissible in a turbid medium;
    an I/O device which encodes a radio frequency signal with information comprised of line delimiters and/or comms data that modulates the current of the source of coherent electromagnetic energy;
    a scanner to direct the beam through the turbid medium and to scan the beam over the target;
    a detector located at a remote location with no physical contact to the source of coherent electromagnetic energy to detect the electromagnetic energy reflected from the target and to output a signal;
    a demodulator to demodulate the output signal from the detector;
    an analog to digital converter to digitize the demodulated output signal from the detector; and
    an image processor to decode the encoded information and convert the digitized signal from the analog to digital converter to a grayscale image.

* * * * *